US006778994B2

(12) United States Patent
Gogolak (10) Patent No.: US 6,778,994 B2
(45) Date of Patent: Aug. 17, 2004

(54) PHARMACOVIGILANCE DATABASE (76) Inventor: Victor Gogolak, 934 Douglass Dr., McLean, VA (US) 22101

( * ) Notice: Subject to any disclaimer, the term of this patent is extended or adjusted under 35 U.S.C. 154(b) by 273 days.

(21) Appl. No.: 09/681,587

(22) Filed: May 2, 2001

(65) Prior Publication Data

US 2002/0165853 A1 Nov. 7, 2002

(51) Int. Cl.[7] ............................. G06F 17/00; G06F 7/00
(52) U.S. Cl. ....................... 707/102; 707/104.1; 704/10
(58) Field of Search ........................... 707/100, 1, 102; 707/205–206; 704/1–10; 715/530–533

(56) References Cited

U.S. PATENT DOCUMENTS

| | | | | |
|---|---|---|---|---|
| 4,384,329 A | * | 5/1983 | Rosenbaum et al. | 704/10 |
| 5,299,121 A | | 3/1994 | Brill et al. | 364/413.01 |
| 5,337,919 A | | 8/1994 | Spaulding et al. | 221/2 |
| 5,371,807 A | | 12/1994 | Register et al. | 382/14 |
| 5,495,604 A | | 2/1996 | Harding et al. | 395/600 |
| 5,502,576 A | | 3/1996 | Ramsay et al. | 358/444 |
| 5,583,758 A | | 12/1996 | McIlroy et al. | 395/202 |
| 5,592,668 A | | 1/1997 | Harding et al. | 395/602 |
| 5,594,637 A | | 1/1997 | Eisenberg et al. | 395/202 |
| 5,634,053 A | | 5/1997 | Noble et al. | 395/604 |
| 5,642,731 A | | 7/1997 | Kehr | 128/630 |
| 5,659,731 A | * | 8/1997 | Gustafson | 707/4 |
| 5,664,109 A | | 9/1997 | Johnson et al. | 705/2 |
| 5,692,171 A | | 11/1997 | Andres | 395/601 |
| 5,737,539 A | | 4/1998 | Edelson et al. | 395/203 |
| 5,758,095 A | | 5/1998 | Albaum et al. | 395/202 |
| 5,804,803 A | | 9/1998 | Cragun et al. | 235/375 |
| 5,833,599 A | | 11/1998 | Schrier et al. | 600/300 |
| 5,845,255 A | | 12/1998 | Mayaud | 705/3 |
| 5,860,917 A | | 1/1999 | Comanor et al. | 600/300 |
| 5,864,789 A | | 1/1999 | Lieberman et al. | 704/9 |
| 5,911,132 A | | 6/1999 | Sloane | 705/3 |
| 5,924,074 A | | 7/1999 | Evans | 705/3 |
| 6,000,828 A | | 12/1999 | Leet | 364/401 |
| 6,014,631 A | | 1/2000 | Teagarden et al. | 705/3 |
| 6,067,524 A | | 5/2000 | Byerly et al. | 705/3 |
| 6,076,083 A | | 6/2000 | Baker | 706/52 |
| 6,076,088 A | | 6/2000 | Paik et al. | 707/5 |
| 6,082,776 A | | 7/2000 | Feinberg | 283/72 |
| 6,108,635 A | | 8/2000 | Herren et al. | 705/2 |
| 6,120,443 A | | 9/2000 | Cohen-Laroque | 600/300 |
| 6,137,911 A | | 10/2000 | Zhilyaev | 382/225 |
| 6,151,581 A | | 11/2000 | Kraftson et al. | 705/3 |
| 6,219,674 B1 | | 4/2001 | Classen | 707/104 |
| 6,226,564 B1 | | 5/2001 | Stuart | 700/231 |
| 6,263,329 B1 | | 7/2001 | Evans | 707/3 |
| 6,446,081 B1 | * | 9/2002 | Preston | 707/104.1 |
| 6,684,221 B1 | * | 1/2004 | Rejndrup | 707/104.1 |

OTHER PUBLICATIONS

Dulong et al., "Method and Apparatus for Dispaying Medication Information", Dec. 6, 2001, U.S. patent application Publication, US Pub. No.: US 2001/0049673 A1.*

(List continued on next page.)

Primary Examiner—Greta Robinson
Assistant Examiner—Susan Rayyan
(74) Attorney, Agent, or Firm—Shaw Pittman LLP (57) ABSTRACT

A system and method for developing a pharmacovigilance database from source data and reference data. The unedited source data contains verbatim terms. The method includes parsing source data into a relational safety database; performing cleanup on the relational safety database; and mapping verbatim terms from the cleaned safety database to at least one token from at least one reference source. Cleanup includes removing redundant entries, correcting misspellings, removing irrelevant non-alpha characters and noise words, and relocating dislocated terms. Mapping verbatim terms to tokens includes nominating tokens from the source data, choosing tokens from the reference sources, and linking chosen tokens to corresponding verbatim terms. In one embodiment, the history of clean-up and mapping is saved as the pedigree of the verbatim-to-token mapping.

20 Claims, 9 Drawing Sheets

OTHER PUBLICATIONS

Multum Trusted Health Information [online], [retrieved on Aug. 22, 2002], 1 p., Retrieved from the Internet: http://www.multum.com.

Epocrates [online], Copyright 2002 [retrieved on Aug. 22, 2002], 1 p., Retrieved from the Internet: http://www.epocrates.com.

PDR.net [online], Copyright 2002 [retrieved on Aug. 22, 2002], 1 p., Retrieved from the Internet: http//www.pdr.net/HomePage_template.jsp.

"VAERS Data: Guide to Interpreting Case Report Information Obtained From the Vaccine Adverse Event Reporting System (VAERS)" [online], [retrieved on Jun. 11, 2002, 2 pp., Retrieved from the Internet: http://www.vaers.org/info.

Szarfman, Ana, M.D., Ph.D., "Application of Screening Algorithms and Computer Systems to Efficiently Signal Combinations of Drugs and Events in FDA's Spontaneous Reports" [online], Oct. 22, 2001, 2 pp., Retrieved from the Internet: http://apha.confex.com/apha/129.am/techprogram/paper_32272.

"Vaccine Adverse Event Reporting System (VAERS)" [online], U.S. Department of Health and Human Services, Jul., 2001 [retrieved Jul., 2001], 12 pp., Retrieved from the Internet: http://www.vaers.org/search/README.

Andrews, Michelle, "Prescription for Disaster," *Smart-Money*, pp. 124–129, May, 2001.

Mootrey, Gina, et al., "Chapter 18: Surveillance for Adverse Events Following Vaccination," *VPD Surveillance Manual*, 20 pp., 1999.

Szarfman, Ana, M.D., Ph.D., "New Methods for Signal Detection," *Proceedings of the 15th International Conference on Pharmacoepidemiology*, 56 pp., Aug. 28, 1999.

DuMouchel, William, "Bayesian Data Mining in Large Frequency Tables, with an Application to the FDA Spontaneous Reporting System," *The American Statistician*, vol. 53, No. 3., 31 pp., Apr., 1999.

"The Totally Unauthorized, Completely Repudiated, Bootlegged, Unsupported, Undocumented, Insider's Post–Pre–Alpha Guide to Multum's Lexicon," Multum Information Services, Inc., pp. 1–49, Copyright 1997–1999, Apr. 12, 1999 (Rev. 3.d).

"Post–Marketing Surveillance for Adverse Events After Vaccination: The National Vaccine Adverse Event Reporting System (VAERS)," *Medwatch*, 12 pp., Nov., 1998.

"Multum Releases Web–Based MediSource Lexicon; Downloadable Drug Product and Disease Listings Database," *PR Newswire*, 2 pp., Apr. 10, 1997.

Lipschutz, Seymour, Ph.D., "Theory and Problems of Linear Algebra," Schaum's Outline Series, McGraw–Hill Book Company, 5 pp., 1968.

Anderson, T. W., "A Bibliography of Multivariate Statistical Analysis," Oliver & Boyd, Edinburgh, 3 pp., 1972.

Darlington, Richard B., "Regression and Linear Models," McGraw–Hill Publishing Company, 15 pp., 1990.

Press, James S. and Wilson, Sandra, "Choosing Between Logistic Regression and Discriminant Analysis," *Journal of the American Statistical Association*, vol. 73, pp. 699–705, Dec., 1978.

Kosko, Bart, "Neural Networks and Fuzzy Systems—A Dynamical Systems Approach to Machine Intelligence," Prentice Hall, Englewood Cliffs, NJ, 11 pp.,1992.

International Search Report for Application No. PCT/US02/13666, dated Jul. 16, 2002 (mailing date).

International Search Report for Application No. PCT/US02/13662, dated Jul. 15, 2002 (mailing date).

\* cited by examiner

| MAP TO | VERBATIM | SOURCE | INCIDENTS | CASE COUNT | QEDRX PROCESSING | | CROSS-REFERENCE | FIRST/LAST REPORTED REACTIONS |
|---|---|---|---|---|---|---|---|---|
| PROZAC | PROZAC | SRS | 47953 | 47937 | | | ORANGE BOOK | APR 27 1969/DEC 2 1997 |
| PROZAC | PROZAC | AERS | 3378 | 3308 | S | | ORANGE BOOK | NOV 1 1997/JUN 29 1999 |
| FLUOXETINE | FLUOXETINE HYDROCHLORIDE | SRS | 2204 | 2203 | | | NDCD TRADENAME | JAN 1 1979/OCT 14 1997 |
| FLUOXETINE | FLUOXETINE | AERS | 574 | 571 | S | | NDCD TRADENAME | NOV 1 1997/JUN 18 1999 |
| PROZAC | PROZAC (FLUOXETINE HYDROCHLORIDE) | AERS | 379 | 378 | | M | ORANGE BOOK | NOV 1 1997/JUN 12 1999 |
| PROZAC | PROZAC (FLUOXETINE) | AERS | 140 | 140 | S | | ORANGE BOOK | NOV 7 1997/APR 24 1999 |
| FLUOXETINE | FLUOXETINE HYDROCHLORIDE | AERS | 122 | 122 | | | ORANGE BOOK | NOV 14 1997/JUN 27 1999 |
| FLUOXETINE | FLUOXETINE (FLUOXETINE HYDROCHLORIDE) | AERS | 65 | 65 | | M | ORANGE BOOK | MAR 1 1998/JUN 24 1999 |
| FLUOXETINE | FLUOXETINE HCL | AERS | 34 | 34 | | | ORANGE BOOK | NOV 1 1997/NOV 1 1998 |
| PROZAC | PROZAC (FLUOXETINE HCL) | AERS | 20 | 20 | | M | ORANGE BOOK | NOV 1 1997/MAR 12 1999 |
| PROZAC | PROZAC (FLUOXETINE HYDROCHLORIDE) | AERS | 17 | 17 | | M | ORANGE BOOK | |
| FLUOXETINE | FLUOXETINE (FLUOXETINE) | AERS | 15 | 15 | | M | ORANGE BOOK | NOV 15 1997/JUN 6 1999 |

FIG. 9

CORRELATION DETAILS
ANALYZED DRUG: CANDESARTAN CILEXETIL
CASE FOR TERM PAIR: RENAL FUNCTION ANALYSES [OTHER REACTION] / RENAL FAILURE AND IMPAIRMENT [OTHER REACTION]

| | | |
|---|---|---|
| 1501 | CASE ID: | 3198047 |
| 1502 | SEX: | F |
| 1503 | AGE: | 57 0 YEARS 0.0 MONTHS |

1504 REACTIONS:

| AS REPORTED | PREFERRED TERM | HIGH LEVEL TERM | HIGH LEVEL GROUP TERM | SYSTEM ORGAN CLASS |
|---|---|---|---|---|
| BLOOD CREATININE INCREASED | BLOOD CREATININE INCREASED | RENAL FUNCTION ANALYSES | RENAL AND URINARY TRACT INVESTIGATIONS AND URINALYSIS | INVESTIGATIONS |
| BLOOD UREA INCREASED | BLOOD UREA INCREASED | RENAL FUNCTION ANALYSES | RENAL AND URINARY TRACT INVESTIGATIONS AND URINALYSIS | INVESTIGATIONS |
| HYPOTENSION NOS | HYPOTENSION NOS | HYPOTENSION | DECREASED AND NON-SPECIFIC BLOOD PRESSURE DISORDERS AND SHOCK | VASCULAR DISORDERS |
| RENAL FAILURE ACUTE | RENAL FAILURE ACUTE | RENAL FAILURE AND IMPAIRMENT | RENAL DISORDERS (EXC NEPHROPATHIES) | RENAL AND URINARY DISORDERS |

1505 CONCOMITANT DRUGS:

| NAME | DOSE | ROUTE | SUSPECT STATUS |
|---|---|---|---|
| ACURETIC | | | YES |
| ATORVASTATIN | | | NO |
| ATACAND | 16 MG QD PO | ORAL | YES |
| CEFIXIME | | | NO |
| NITRO-DUR | | | NO |
| TERBASMIN EXPACTORANTE | TAB QD | | NO |

| | | |
|---|---|---|
| 1506 | OUTCOMES: | HOSPITALIZATION - INITIAL OR PROLONGED (HO) LIFE - THREATENING (LT) |
| 1507 | MANUFACTURER CONTROL CODE: | 19990200143 |
| 1508 | MANUFACTURER DATE: | 1999-03-5 |
| 1509 | ADVERSE EVENT DATE: | 1998-12-13 |
| 1510 | REPORT TYPE: | EXP |
| 1511 | REPORT SOURCE: | OTH |
| 1512 | CASE SOURCE: | AERS |
| 1513 | NARRATIVE: | |

PHARMACOVIGILANCE DATABASE

CROSS REFERENCE TO RELATED APPLICATIONS

This application is related to the following co-pending applications, each filed May 2, 2001, and incorporates the disclosure of these applications by reference in their entirety: A Method and System for Analyzing Drug Adverse Effects U.S. patent application Ser. No. 09/681,585; A Method and System for Web-Based Analysis of Drug Adverse Effects U.S. patent application Ser. No. 09/681,583; Method and System for Graphically Depicting Drug Adverse Effects Risk U.S. patent application Ser. No. 09/681,586; A Method and System for Analyzing Drug Adverse Effects Employing Multivariate Statistical Analysis U.S. patent application Ser. No. 09/845,722.

BACKGROUND OF INVENTION

1. Field of the Invention

The present invention relates generally to systems and methods for developing a pharmacovigilance database from source data, both publicly available and privately developed, and reference data.

2. Description of the Related Art

In September 1997, information regarding cardiopulmonary disease related to the use of fenfluramine and phentermine ("fen-phen") prompted the United States Food and Drug Administration (FDA) to request the manufacturers of these drugs to voluntarily withdraw both treatments for obesity from the market. Subsequent studies show a 25 percent incidence of heart valve disease apparently resulting from diet drug use. Thus, up to 1,250,000 people may have sustained heart valve damage from these diet drugs and the FDA indicates that this may be the largest adverse drug effect they have ever dealt with.

Under existing federal regulations, post-marketing safety reports are be submitted to the FDA for serious and unexpected adverse experiences from all sources (domestic and foreign); and spontaneously reported adverse experiences that occur domestically and that are: serious and expected; or non-serious and unexpected; or non-serious and expected.

To facilitate reporting and data analysis, the FDA created the Spontaneous Reporting System (SRS), a pharmacovigilance database. The SRS contains adverse drug reaction reports from a variety of sources over a period covering 1969 through 1997. This data is available in an ASCII flat file from the FDA. However, the flat file, by its nature is not a relationally structured database amenable to typical query.

Over the past several years (1997 2001), the FDA has implemented a follow-on system to SRS, i.e., the Adverse Event Reporting System (AERS). AERS is a non-cumulative database of post-market drug adverse events. Its purpose is to serve as an early warning indicator or signaling system for adverse drug reactions not detected during pre-market testing. The data, without a search engine, is available on CD ROM from the federal government in a combination of ASCII delimited flat file and SGML format. The files include: demographic and administrative information; along with drug, reaction, patient outcome, and source for each case.

Beyond SRS and AERS, pharmaceutical companies, hospitals, and other entities have also been known to track adverse drug effects; often using unique database structures. The existence of these various databases using different structures presents an obstacle to efficient use of potentially valuable data. As with SRS and AERS, database structure can vary within an organization over time, and also between concurrent adverse event databases. Such variability makes it cumbersome to query across databases.

In addition, differing terminology employed by disparate databases also make conventional queries cumbersome and the results unreliable. This problem is acute in the area of medical information related to substances such as drugs. Drugs and other prescription and non-prescription therapeutic substances may be known by a variety of names. In addition to the chemical name, many drugs have several clinical names recognized by health care professionals in the field. It is not uncommon for a drug to have several different trade names depending on the manufacturer. This matter is further complicated by one or more functional names that may be associated with a drug or other substance. For example, an antidepressant may be Prozac, a fluoxetine, a serotonin reuptake inhibitor, or a serotonin receptor specific modulator. However, antidepressants include many other drugs, such as lithium and other catecholaminergic drugs, and there are serotonin reuptake inhibitors in addition to Prozac. Even "standardized" terminology can differ between databases. For example, some adverse event databases request reaction terminology consistent with the Medical Dictionary for Regulatory Activities (MedDRA™), while other databases request, or already contain, input consistent with World Health Organization Adverse Reaction Terminology (WHO-ART) or Coding Symbols for a Thesaurus of Adverse Reaction Terms (COSTART) developed and maintained by the FDA's Center for Drug Evaluation and Research.

Further, data corruption in databases such as SRS and AERS is acknowledged, but not quantified, by the proponents. Data corruption at the database field level can include extraneous non-alpha characters, noise words, misspellings, and dislocations (e.g., data that is valid for one field, erroneously entered into another, inappropriate field). Databases that allow entry of free text information are especially susceptible to data corruption. At a higher level, existing adverse event databases have been known to contain redundant cases documenting the same adverse event.

U.S. Pat. No. 5,634,053 to Noble et al., "Federated Information Management (FIM) System And Method For Providing Data Site Filtering And Translation For Heterogeneous Databases" discloses an information management system that integrates data from a plurality of interconnected local databases to provide users with access to a virtual database. The system includes a user interface for generating a global query to search the virtual database, a smart dictionary database that contains configuration data, a data information manager that decomposes the global query into local queries, and a plurality of local information managers that execute the local queries to search for and retrieve data from the enumerated databases. A filter generates a list of those local databases that contain information relevant to the global query. As a result, the data information manager only generates local queries for the enumerated local databases. An input translator converts the global query into the respective local formats for the local databases so that the system provides true integration of heterogeneous databases. An output translator converts the data retrieved from each local database into a uniform input/output format so that the data presented to the user is integrated. The user typically selects the input/output format as his or her local format or a global format associated with the virtual database.

U.S. Pat. No. 5,664,109 to Johnson et al., "Method For Extracting Pre-Defined Data Items From Medical Service Records Generated By Health Care Providers" discloses a central medical record repository for a managed health care organization that accepts and stores medical record documents in any format from medical service providers. The repository then identifies the document using information automatically extracted from the document and stores the extracted data in a document database. The repository links the document to a patient by extracting from the document demographic data identifying the patient and matching it to data stored in a patient database. Data is extracted automatically from medical records containing "unstructured" or free form text by identifying conventional organization components in the text and is organized by executing rules that extract data with the aid of such information. Documents for a patient are retrieved by identifying the patient using demographic data.

U.S. Pat. No. 5,845,255 to Mayaud, "Prescription Management System" discloses a wirelessly deployable, electronic prescription creation system for physician use which captures into a prescription a patient condition-objective of the prescribed treatment and provides for patient record assembly from source elements, with privacy controls for patient and doctor, adverse indication review and online access to comprehensive drug information including scientific literature. Extensions to novel multi-drug packages and dispensing devices, and an "intelligent network" remote data retrieval architecture as well as onscreen physician-to-pharmacy and physician-to-physician e-mail are also provided.

U.S. Pat. No. 5,911,132 to Sloane, "Method (Of) Using (A) Central Epidemiological Database" discloses a method in which patient disease is diagnosed and/or treated using electronic data communications between not only the physician and his/her patient, but via the use of electronic data communications between the physician and one or more entities which can contribute to the patient's diagnosis and/or treatment, such electronic data communications including information that was previously received electronically from the patient and/or was developed as a consequence of an electronic messaging interaction that occurred between the patient and the physician. Such other entities illustratively include a medical diagnostic center and an epidemiological database computer facility that collects epidemiological transaction records from physicians, hospitals, and other institutions that have medical facilities, such as schools and large businesses. The epidemiological transaction record illustratively includes various medical, personal, and epidemiological data relevant to the patient and his/her present symptoms, including test results, as well as the diagnosis, if one has already been arrived at by the e-doc. The epidemiological database computer facility can correlate this information with the other epidemiological transaction records that it receives over time in order to help physicians make and/or confirm diagnoses as well as to identify and track epidemiological events and/or trends.

U.S. Pat. No. 5,924,074 to Evans, "Electronic Medical Records System" discloses a medical records system that creates and maintains all patient data electronically. The system captures patient data, such as patient complaints, lab orders, medications, diagnoses, and procedures, at its source at the time of entry using a graphical user interface having touch screens. Using pen-based portable computers with wireless connections to a computer network, authorized healthcare providers can access, analyze, update, and electronically annotate patient data even while other providers are using the same patient record. The system likewise permits instant, sophisticated analysis of patient data to identify relationships among the data considered. Moreover, the system includes the capability to access reference databases for consultation regarding allergies, medication interactions, and practice guidelines. The system also includes the capability to incorporate legacy data, such as paper files and mainframe data, for a patient.

U.S. Pat. No. 6,076,088 to Paik et al., "Information Extraction System And Method Using Concept Relation Concept (CRC) Triples" discloses an information extraction system that allows users to ask questions about documents in a database, and responds to queries by returning possibly relevant information that is extracted from the documents. The system is domain-independent, and automatically builds its own subject knowledge base. It can be applied to any new corpus of text with quick results, and no requirement for lengthy manual input. For this reason, it is also a dynamic system that can acquire new knowledge and add it to the knowledge base immediately by automatically identifying new names, events, or concepts.

U.S. Pat. No. 6,128,620 to Pissanos et al., "Medical Database For Litigation" discloses a medical database and associated methods that are especially suited for compiling information in a medical malpractice situation. A general medical database is provided and specific medical information corresponding to a given situation is entered. Entry of the information automatically cross-references some terms of the entered data to definitions in the general medical database. Terms are readily looked up when reviewing specific medical information and definitions are easily inserted where desired. A drug reference display provides two-way lookup from drugs to their side effects (or contraindications or interactions) and back. Significant information from an entered medical chronology is easily copied to a significant information section when a reviewer finds the information important.

U.S. Pat. No. 6,219,674 to Classen, "System for creating and managing proprietary product data" discloses systems and methods for creating and using product data to enhance the safety of a medical or non-medical product. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population sub-groups. The system may also be programmed to incorporate the information into intellectual property and contract documents. Manufacturers can include the information in consumer product information that they provide to consumers or, in the case of certain medical products, prescribers of the medical products.

None of the above references, alone or in combination, addresses improving the quality of the underlying verbatim adverse drug event data. Nor do the references address mapping this underlying data to accepted pharmaceutical community terms and hierarchies. Specifically, the references do not address parsing of flat file adverse drug event data into a relational database structure to support efficient query. The problem of differing terminology in the data fields of disparate databases also remains un-addressed; as does the problem of data corruption in the form of misspelling and extraneous characters, along with resolution of redundant cases.

In view of the above-described deficiencies associated with data concerning drugs and other substances associated with medical databases, especially known adverse event databases, there is a need to solve these problems and enhance the quality and accuracy of such data. These enhancements and benefits are described in detail herein below with respect to several alternative embodiments of the present invention.

SUMMARY OF INVENTION

The present invention in its several disclosed embodiments alleviates the drawbacks described above with respect to existing adverse event databases and incorporates several additionally beneficial features.

In a preferred embodiment, the present invention is a method for developing a pharmacovigilance database from source data and reference data. The unedited source data contains verbatim terms. The method includes parsing source data into a relational database; performing cleanup on the relational database; and mapping verbatim terms from the cleaned database to at least one token from at least one reference source.

Cleanup includes removing redundant entries, correcting misspellings, removing irrelevant non-alpha characters and noise words, and relocating dislocated terms. When the source or reference data spans more than one generation, preferred embodiments standardize and map historical terms to current terms. Where the choice of the reference data is itself an option, preferred embodiments incorporate a method for selecting the reference data source and the automatically propagated correction and mapping rules associated with that choice. Mapping verbatim terms to tokens includes nominating tokens from the source data, choosing tokens from the reference sources, and linking chosen tokens to corresponding verbatim terms. In one embodiment, the history of clean up and mapping is saved as the pedigree of the verbatim-to-token mapping.

It will be appreciated that such a system and method for developing a pharmacovigilance database is advantageous to the various risk assessors in the pharmaceutical field. Pharmaceutical industry personnel would have higher quality data (i.e., more current, complete, and accurate data) with which to monitor and manage drugs in the marketplace. Marketing and sales personnel could employ such a database to understand and position a drug to optimum advantage to patients and physicians. Research & development personnel could assess drugs planned for market introduction in light of adverse event reports of other drugs in the same chemical or therapeutic class. Regulators and the public could benefit from increased quality date available as a basis for labeling drugs.

It is an object of the present invention to integrate disparate adverse drug effect databases into a structure amenable to efficient query.

It is a further object of the present invention to mitigate the effect of data corruption on adverse drug event databases.

It is an object of the present invention to develop an adverse drug effect database amenable to query using canonical terms accepted in the pharmaceutical industry. Linking cases to standard vocabulary for data such as drug name and reaction enables meaningful statistical comparisons to be made.

The beneficial effects described above apply generally to the exemplary systems and methods for developing a pharmacovigilance database. The specific structures through which these benefits are delivered will be described in detail hereinbelow.

BRIEF DESCRIPTION OF DRAWINGS

The invention will now be described in detail, by way of example without limitation thereto and with reference to the attached figures.

DETAILED DESCRIPTION

As required, detailed preferred embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Figure 1:
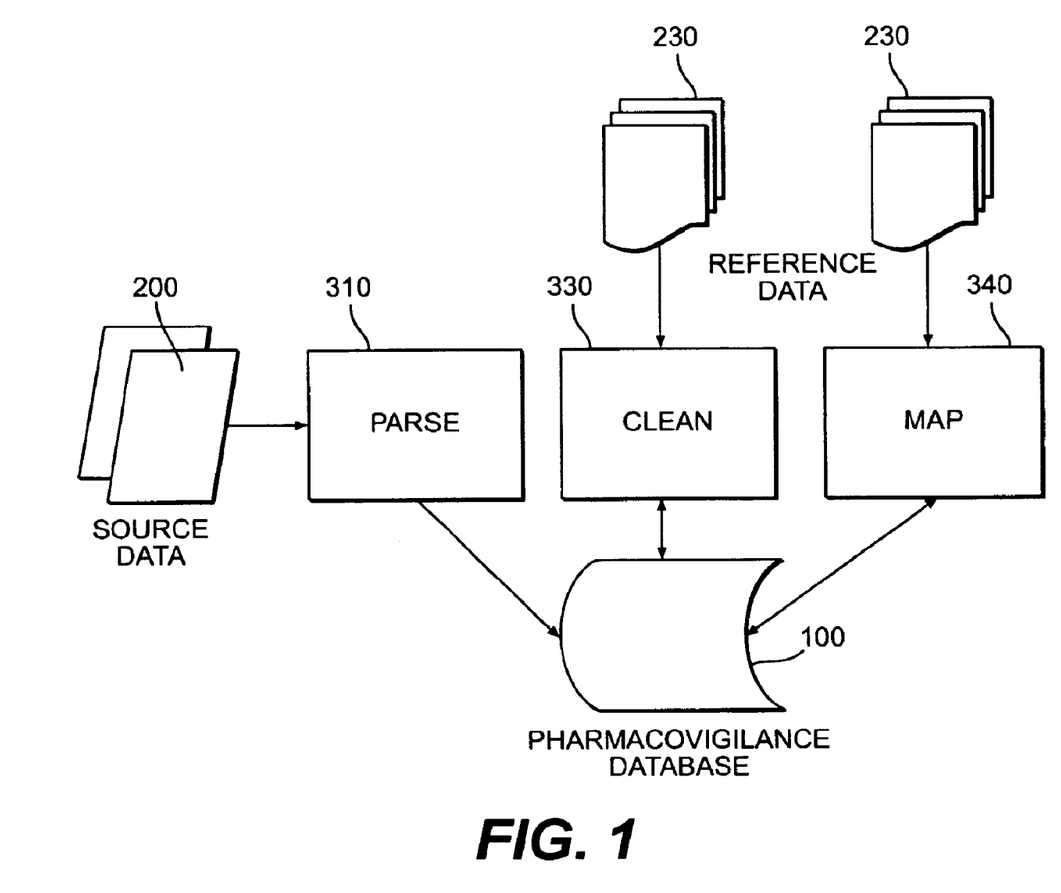
FIG. 1 illustrates a method of the present invention for development of a pharmacovigilance database.

Referring to FIG. 1, the present invention includes a preferred method for developing a pharmacovigilance database 100 from source data 200. The method includes the steps of parsing 310 source data 200 into a relational database structure, performing cleanup 330 on the parsed data, and mapping 340 cleaned parsed source data to reference data 230. While the preferred methods of the present invention parse source data 200 prior to performing cleanup 330, cleanup 330 can be performed independently of, and prior to, parsing. In one embodiment, the source data 200 is already in a relational database structure amenable to embodiments of the present invention.

Figure 2:
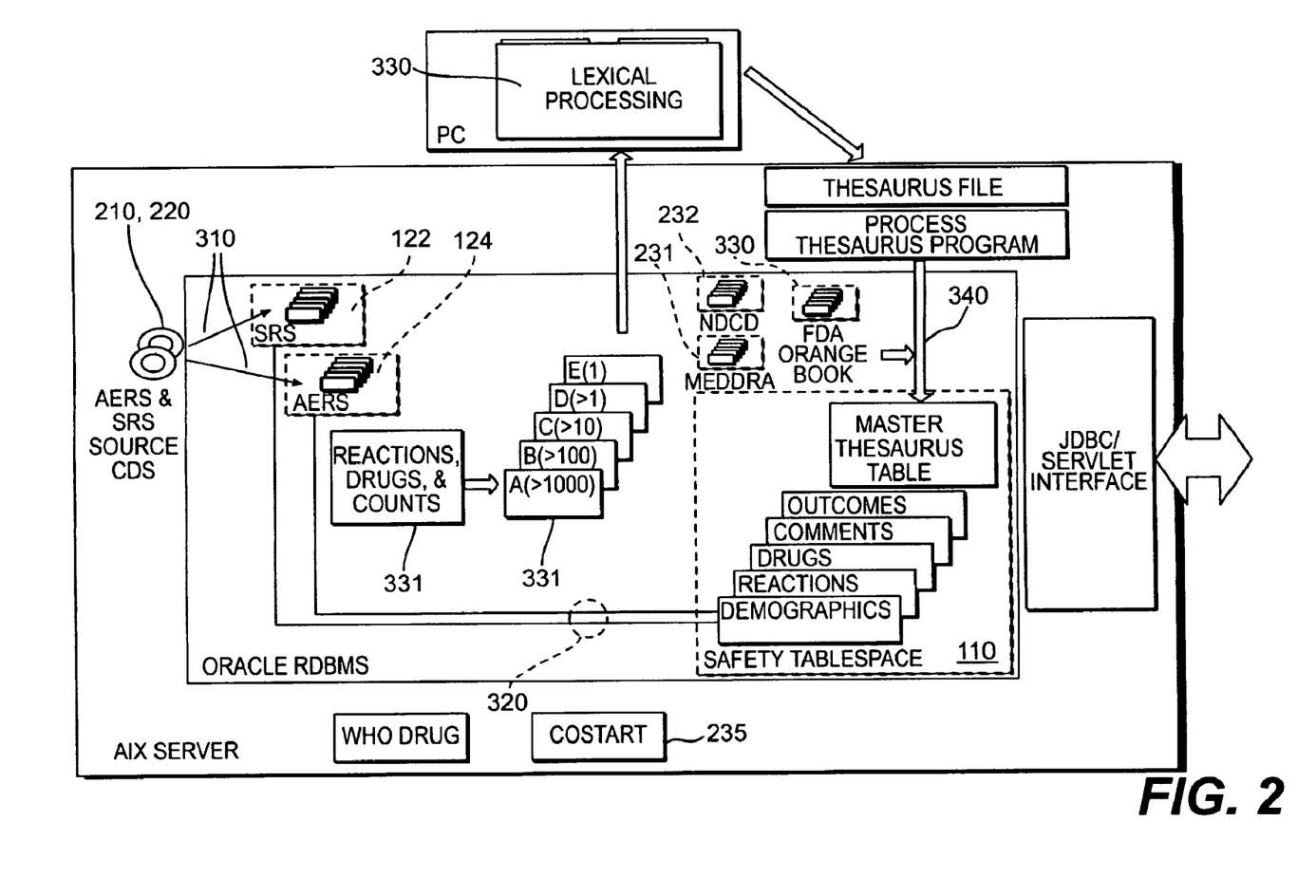
FIG. 2 illustrates a specific implementation of a pharmacovigilance database of the present invention.

Referring to FIG. 2, a specific implementation of a preferred method of the present invention is illustrated. In this embodiment, the source data includes, but is not limited to, SRS 210 and AERS 220. In addition to demographic information, AERS and SRS call for reports on outcomes, report source, and concomitant drugs. Other data and sources (domestic, foreign, or international in scope) can serve as inputs to the process. Preferred embodiments accommodate adverse event data from pharmaceutical corporations, hospitals; physicians, and health insurers; along with data from state, federal, and international agencies. The primary sources of the pharmaceutical industry data are individual adverse event databases of the pharmaceutical corporation safety departments. In each case, source data may be focused on clinical trails, post-market surveillance, research databases, or the like. The unedited data in each source database is referred to as "verbatim." In addition to source data, reference data from accepted canonical references, e.g., MedDRA™ 231, National Drug Code Directory 232, and FDA Orange Book 233, is used in preferred embodiments of the present invention. Preferred embodiments of the invention also link to genomic and proteomic data. Preferred embodiments of the invention provide means to substitute and manage both source and reference data.

The method illustrated in FIG. 2 includes parsing 310 source data 210, 220 into a relational database structure. For data sources such as SRS and AERS not already in a relational database structure, transformation from raw source data 210, 220 to a relational structure preferably includes parsing each data source into an image 122, 124 with fields tailored to its corresponding source. Subsequently, the images 122, 124 are consolidated 320 into a single safety tablespace 110. Since the database can be simple or complex, the present invention provides the ability to add many "dimensions" (e.g., age, sex, dates, reactions, doses, outcomes, report source, concomitant drugs): some structured, some narrative, some numerical, and many categorical variables such as reaction. Hierarchies in all dimensions (in both preferred and custom paths) are definable as required by the particular end user.

Since several of the most favored data sources are not published in a format that lends itself to direct query, e.g., SRS is available from the U.S. Government only as delimited ASCII data, parsing such data in to a relational database model allows the use of leveraging data management tools which are ineffective on flat files. In preferred embodiments of the present invention, the safety tablespace 110 provides a common set of fields for the parsed source data 122, 124.

Data cleanup may be performed independently of parsing source data into a safety database. This allows cleanup to be continual, ongoing, and iterative; either before or after one or more source databases are processed into the pharmacovigilance database. Adverse event database cleanup is an incremental process, proceeding from automated cleanup of certain errors, through human-assisted cleanup of ambiguous entries, to human correction of identified gross errors. Specific cleanup tasks include noise reduction (e.g., suppression of non-alpha characters noise words, and combination words); adjustment for misspellings; adjustment for dislocations, and resolution of possible redundant entries. In the preferred embodiment illustrated in FIG. 2, reactions, drugs, and counts of the occurrence (by case and absolute) of each are extracted 331 from the parsed AERS data 124. The counts are then grouped 331; in this embodiment, grouping is by order of magnitude of the count. In the preferred embodiment illustrated in FIG. 2, the bulk of data cleanup 330 is performed on a computing platform separate from database storage. A spreadsheet application, such as Microsoft Excel is used to track cleanup operations. For example, the first column in such a spreadsheet may contain the verbatim term; the second column may contain a noise-suppressed verbatim term; the fourth column may contain the spell-checked verbatim term, and so on. Other data cleanup applications, such as Metaphone (discussed infra), also reside on this separate computing platform in the illustrated embodiment. However, cleanup applications need not reside on a separate computing platform, or may be accessible via the Internet or other computer network. Noise reduction involves suppression of words and characters that are typically unnecessary in determining the correct name for drug or reaction verbatim. Noise words and characters include, but are not limited to non-alpha characters (such as numbers, diacriticals, brackets, and control characters), words (e.g., "mg" or "tablet"), combination words (e.g., "20 mg" with no space). For example, both "Tylenol (500 mg)" and "Tylenol Capsules" would be reduced to "Tylenol." A list of noise words and noise punctuation is stored in database tables associated with lexical processing. Non-alpha characters, such as control characters, are also suppressed at this stage.

After noise reduction, misspellings are detected and adjusted for using known tools such as spell checkers, sound-alike suggestion programs, a verbatim replacement table, and human inspection.

A preferred spell checker operates on noise-suppressed verbatim terms, making a series of spelling variations on terms not found in the reference sources. These variations are used as the basis for searching reference sources and suggesting candidate canonical terms. Reference sources include standard and special-purpose dictionaries. The variations introduced include: adding an extra character to the term, e.g., allowing noise-suppressed verbatim such as "proza" to be searched as "Prozac;" removing a character from the term, e.g., allowing noise-suppressed verbatim such as "prozzac" to be searched as "Prozac;" swapping adjacent characters, e.g., allowing noise-suppressed verbatim such as "rpozac" to be searched as "Prozac." In addition to a spelling suggester, a sound-alike program, such as Metaphone or Soundex is employed to suggest variations. Metaphone is a published algorithm similar to Soundex. It was originally published in the December 1990 issue of Computer Language magazine. Every word has a four-letter Metaphone value that can be calculated. The Metaphone suggester calculates the Metaphone value for each entry in the reference sources and for each unresolved verbatim term. Those reference source terms having a Metaphone value matching that of an unresolved verbatim term will be offered as a suggestion to a database developer for resolution. For example, the Metaphone value for both "prosac" and "prozack" is PRSK; the Metaphone value for both "Claritin" and "Klariton" is "KLRT." Where no candidates satisfy the developer, an option is provided for accepting a surrogate term from the developer.

Preferred embodiments of the invention include steps for capturing and using domain-specific lexical knowledge not easily applied through noise reduction or spell checking. At the basic level, this amounts to use of a replacement table, containing mappings from known errors to corrected canonical terms. On a more sophisticated level, as domain-specific knowledge is accumulated, autocoders are employed to capture human decision-making experience regarding cleanup.

Human interaction is particularly useful in identification and correction of dislocation errors, i.e., where a term valid in one field (e.g., headache/reaction) appears in a field where it is not valid (e.g., headache/drug). Dislocation errors are identified in preferred embodiments of the present invention where a term does not fit the type of the field it is found in, but nonetheless exists in reference sources outside the scope of the particular field.

Redundant entries are identified and removed with operator assistance. A "case" includes all data regarding the adverse events experienced by one person, taking a drug. A sequence of events regarding a person, taking a drug should not be recorded as separate cases (potentially duplicating the adverse events associated with the case). This is important for correct statistical views of the data. The present invention provides tools to operators for identification and consolidation redundant cases. In preferred embodiments of the present invention, multiple cases involving the same person over a contiguous period are presented to an operator for a determination whether or not such entries actually represent one case with multiple (or possibly single-occurrence, multiple-reported) events.

If a case concerning an "eye pain" reaction is amended fifteen times, only one instance of eye pain should be aggregated for this individual case. Through record linking, preferred embodiments of the present invention match successor reports with their predecessors using data inherent in the records, and comparing other information in the records to gauge the quality of the match. For example, two cases may match on "case identification" field, or a "drug manufacturer identification" field, or a "report date." Those cases known to be redundant, and those cases showing a link between records are presented to researchers for resolution. In alternate embodiments, resolution between likely redundant cases is accomplished via an expert system.

Note that the underlying verbatim terms are not changed by application of noise suppression, the use of spell checkers, the resolution of dislocations, or the resolution of redundant entries. Verbatim terms, e.g., drug and reaction terms, that have been parsed into a safety database and cleaned, are mapped to "tokens" from the reference data sources. The word "token" refers to the specific term(s), from one of more of the reference sources, that is associated with one or more verbatim terms in a fashion that allows a search for the token to return results containing the verbatim term(s) linked to the token. Where an exact match exists between a verbatim term (source or cleaned) and a reference term, the verbatim term is mapped to the reference term as token. Where no exact match is found between verbatim (cleaned or otherwise) and reference data terms, preferred embodiments of the present invention present a series of steps for resolving such unmatched terms.

In addition to corruption in verbatim data, valid variations in terminology may also be resolved through mapping to reference data tokens. For example, "PROZAC" and other trade names for flouxetine are preferably mapped to the generic "flouxetine." In another example, luliberin, gonadotropin releasing hormone, GnRH, gonadotropin releasing factor, luteinizing hormone releasing hormone, LHRH, and LH-FSH RH are equivalents and may be considered as such for analyzing adverse effects. Furthermore, different chemical derivatives, such as acidic or basic forms of the same drug may be grouped together, where a reference data term exists, under the same token in order to analyze adverse drug events. In some embodiments of the invention, source data verbatim terms are nominated as token candidates; frequency of occurrence and absolute count being typical bases for nominating a term as a token candidate. In FIG. 2, verbatim drug and reaction terms are grouped by order of magnitude of absolute count 331. For reactions, token candidates are chosen from accepted reference sources such as MedDRA, COSTART, and WHOART. For drugs, token candidates are chosen from corresponding canonical sources such as the National Drug Code Directory (NDCD), WHODRUG, and the Orange Book. Individual verbatim terms are then mapped to the selected tokens. In preferred embodiments, this process is used for multiple database dimensions in addition to drug and reaction, e.g., outcomes where the definition of "serious" outcomes can differ over time and between reference sources. This mapping enables those searches of the pharmacovigilance database focused on tokenized fields, e.g., drug and reaction fields, to be executed with greater confidence. Using the mapping approach, variability in adverse event data entry, typically a difficult-to-control aspect of data collection on a large scale, is mitigated as a source of error.

Figure 3:
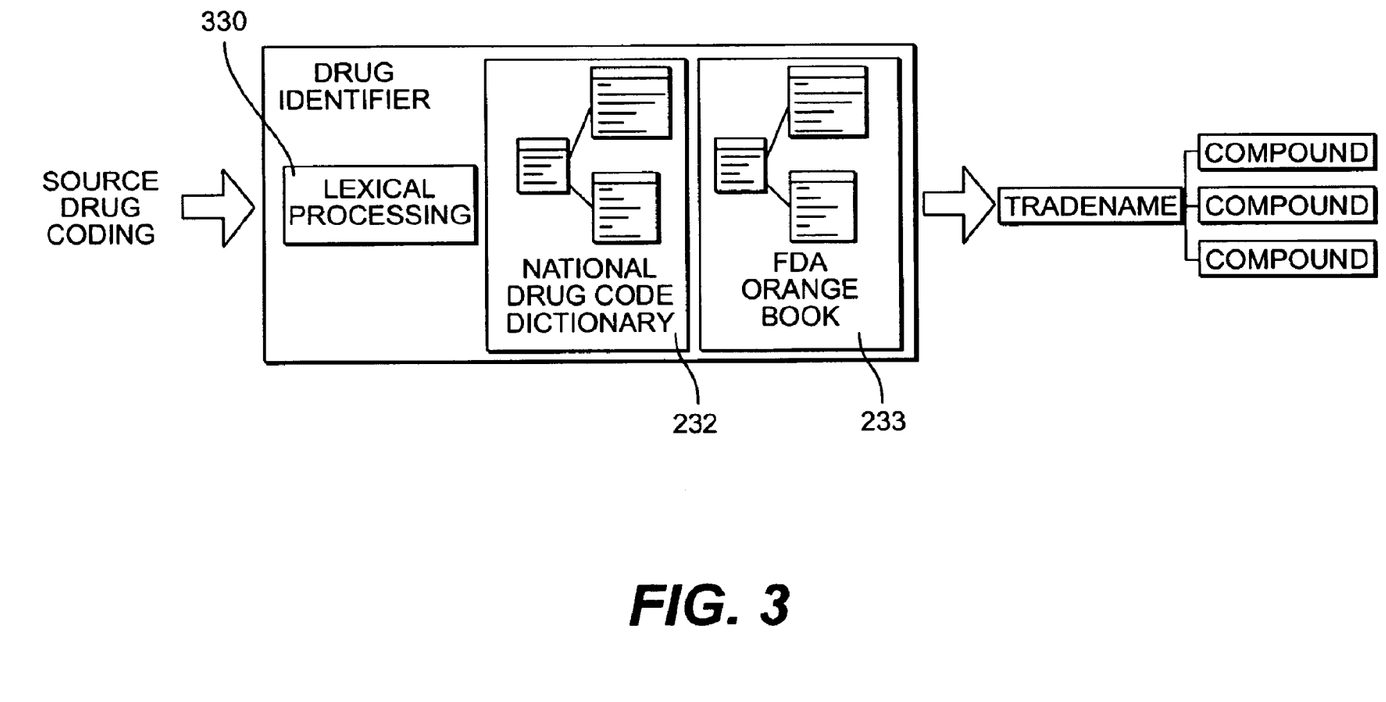
FIG. 3 illustrates mapping of cleaned verbatim source data drug terms to trade and generic canonical terms from the National Drug Code Directory and the Food and Drug Administration Orange Book.
Figure 4:
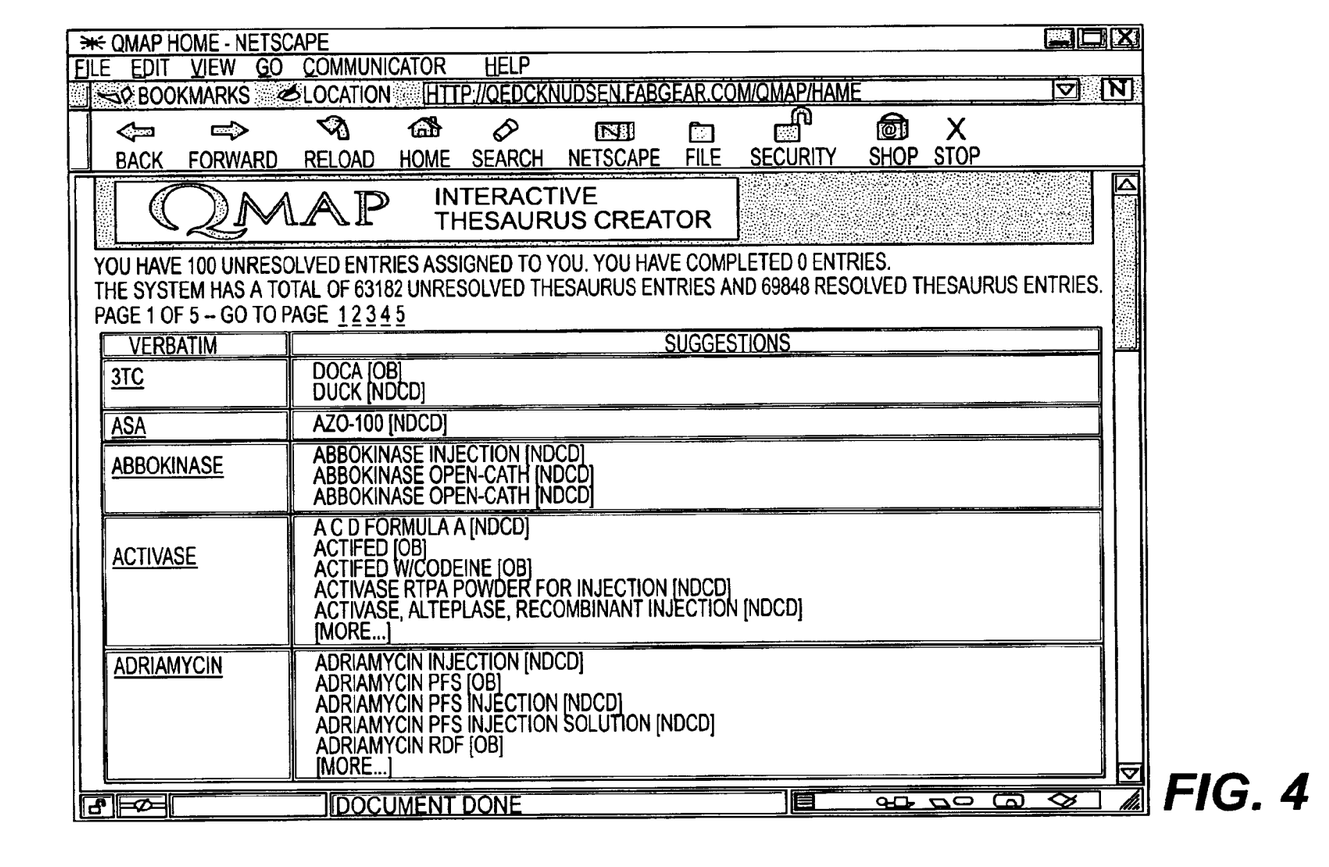
FIG. 4 is a sample window illustrating how a list of unresolved drug verbatim are presented to an operator along with suggestions for resolution.
Figure 5:
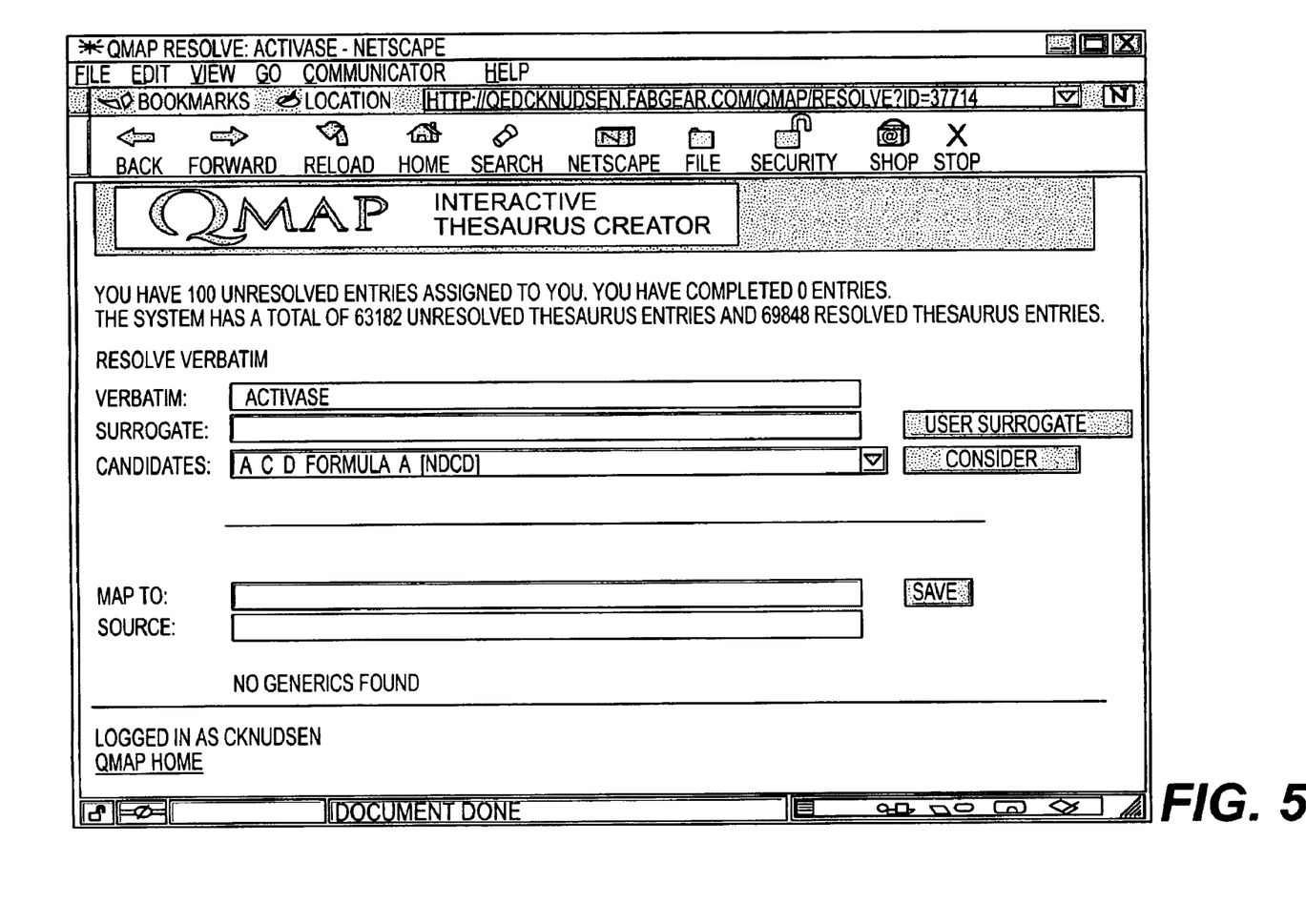
FIG. 5 is a sample window illustrating how an individual unresolved drug verbatim entry may be presented to an operator
Figure 6:
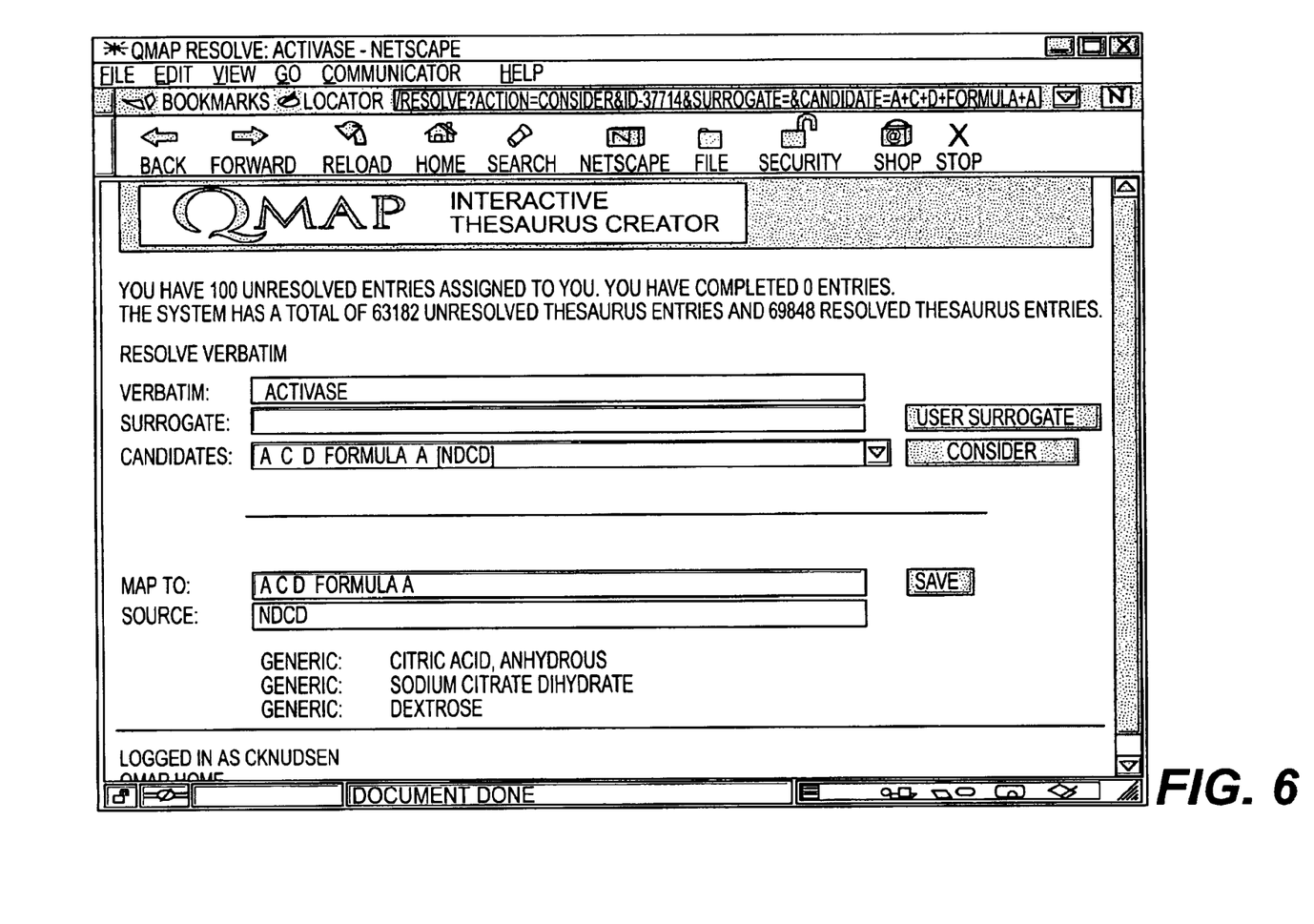
FIG. 6 is a sample window illustrating how an operator may effect resolution of an unresolved drug verbatim entry.

FIG. 2 indicates a stage for mapping 340 SRS and AERS corrected verbatim to NDCD 232, MedDRA, 231 and Orange Book 233 canonical terms and structures. As noted earlier, where an exact match exists between a verbatim term (source or cleaned) and a reference term, the verbatim term is mapped to the reference term as token. Where no exact match is found between verbatim (cleaned or otherwise) and reference data terms, preferred embodiments of the present invention present a series of steps for resolving such unmatched terms. FIG. 3 illustrates mapping of cleaned 330 source data verbatim drug terms to trade names, and generic/compound names found in NDCD 232 and the FDA Orange Book 233. FIG. 4 is a sample interactive screen for resolving non-exact matches. In this sample screen, a user is presented with a number of assigned unresolved entries. Preferred embodiments of the invention present the user with any suggestions identified by lexical processing (e.g., Metaphone, fixed list) for each unresolved verbatim term. The user may then select from this list or, as illustrated in FIG. 5, enter a surrogate term. After selecting a candidate term (or entering a surrogate term and choosing "consider surrogate"), a list of generic drug names will be shown (if the matched term was indeed a trade name rather than a generic). As illustrated in FIG. 6, at this point, a user can either save the mapping or modify the list of generic terms. This last option will allow a user to override the list of generics.

Figure 7:
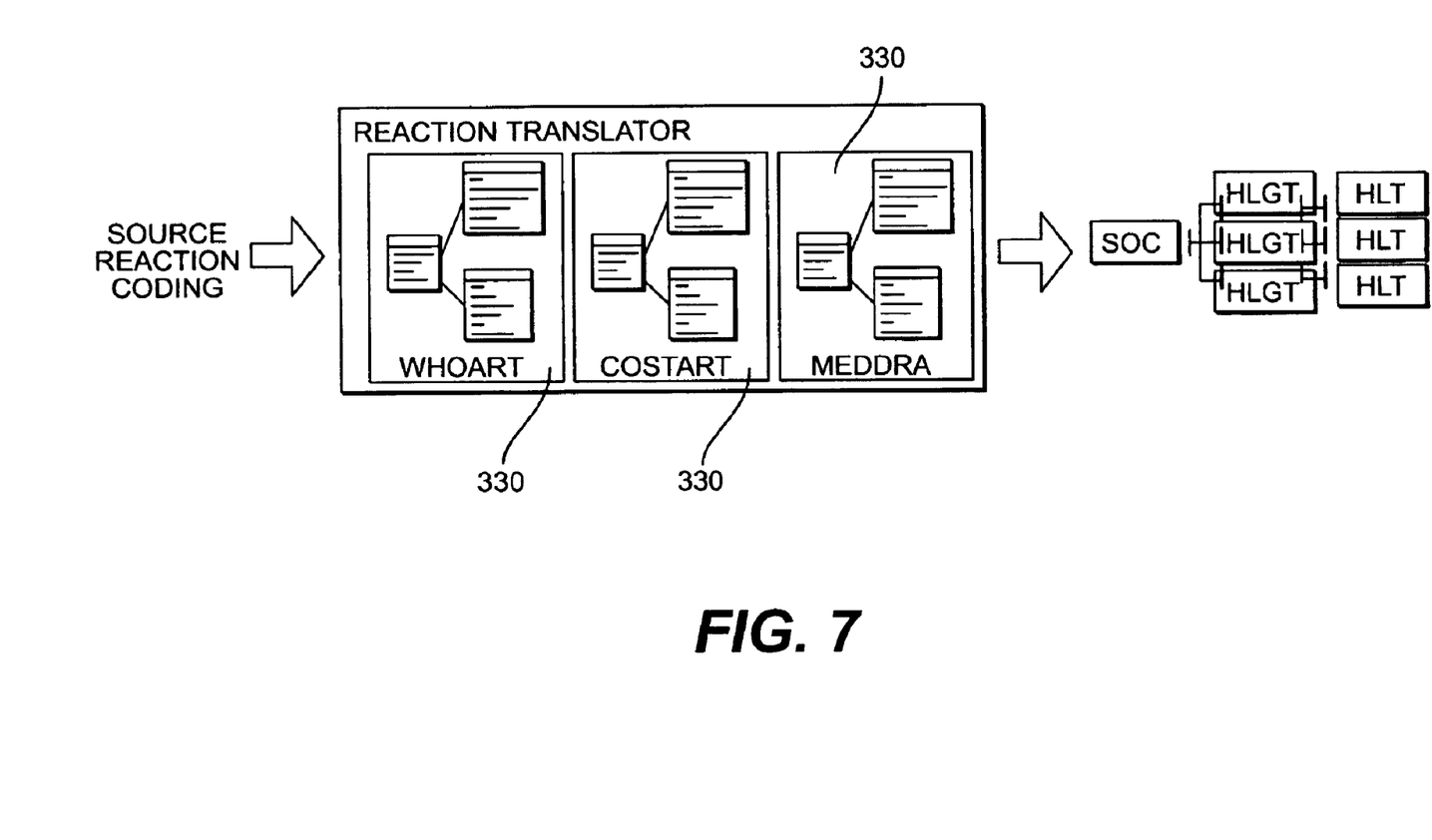
FIG. 7 illustrates mapping of cleaned verbatim source data reaction terms to WHOART, COSTART and MedDRA reaction terms and hierarchies.

FIG. 7 illustrates mapping of cleaned source data reaction terms to standardized hierarchies such as WHOART 234, COSTART 235, and MedDRA 231. Specifically, cleaned source data reaction terms are mapped to multiple levels (and possibly multiple entries within a level) of the hierarchy. In preferred embodiments, mapping of cleaned verbatim reaction terms proceeds in a fashion similar to mapping of drug terms. Also note that while the illustrated preferred embodiments perform mapping on cleaned source data, mapping may be performed on uncleaned (or even unparsed) source data. Transparency in the process of moving from source data verbatim terms to a cleaned safety database with verbatim terms mapped to tokens is important to both database developers/operators and to end users. Preferred embodiments of the present invention capture the way source data terms have been cleaned and mapped as the "pedigree" of each term. The "pedigree" of a term is the link between the mapped term and the decisions made during data cleanup. End users typically wish to verify the pedigree of the data they use. In those embodiments, retained data includes one or more of the following as appropriate: verbatim term, token mapped to, source of the verbatim term, number of occurrences of the verbatim term, number of cases in which the verbatim term appears, which type of cleanup (if any) was performed, a cross-reference to where the token is defined, and dates of the earliest and latest reported occurrence.

Figure 8:
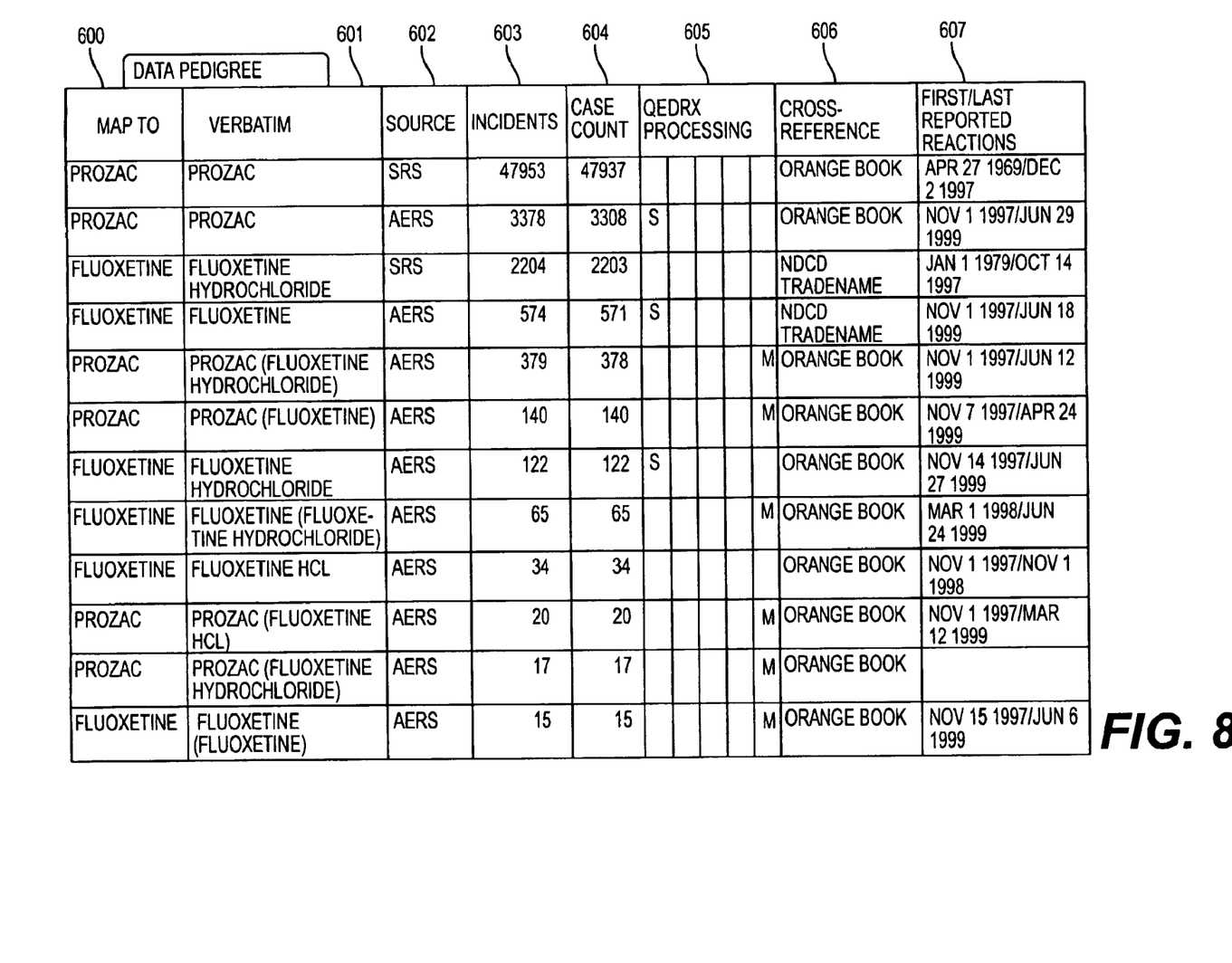
FIG. 8 illustrates mapping of source data drug terms to reference source "map to" tokens.

An exemplary pedigree screen from an illustrative embodiment of the invention disclosed in a related patent application is presented in FIG. 8. The screen illustrates the nature of mapping in accordance with the present invention, and a manner in which the pedigree of a drug term can be used. Referring to the fourth entry from the bottom of FIG. 4 as an example, the "Map To" column 600 shows generic name or trade name token, e.g., "PROZAC" to which the "Verbatim" 601 term, e.g., "Fluoxetine Hcl" is mapped. The verbatim term can be any form of the name under which this drug was found in the "Source" 602, e.g., "AERS" data, including misspellings, variations, etc. The "Incidents" column 603 represents the number of times the verbatim terms occurs in the indicated source data, while the "Case Count" column 604 discloses the number of case in which the verbatim term appears in the source data. The "QEDRx Processing" column 605 indicates the type of cleanup that has been performed on the data. In this particular embodiment, the sub-columns in order under "QEDRx Processing" indicate: spelling correction, noise word correction; combo word correction; removal of numerics; and removal of marks. The "Cross-Reference" column 606 indicates which reference source the "Map To" term is associated with. Finally, "First/Last Reported Reactions" 607 indicates the date range from the earliest to latest cases containing the verbatim term.

Figure 9:
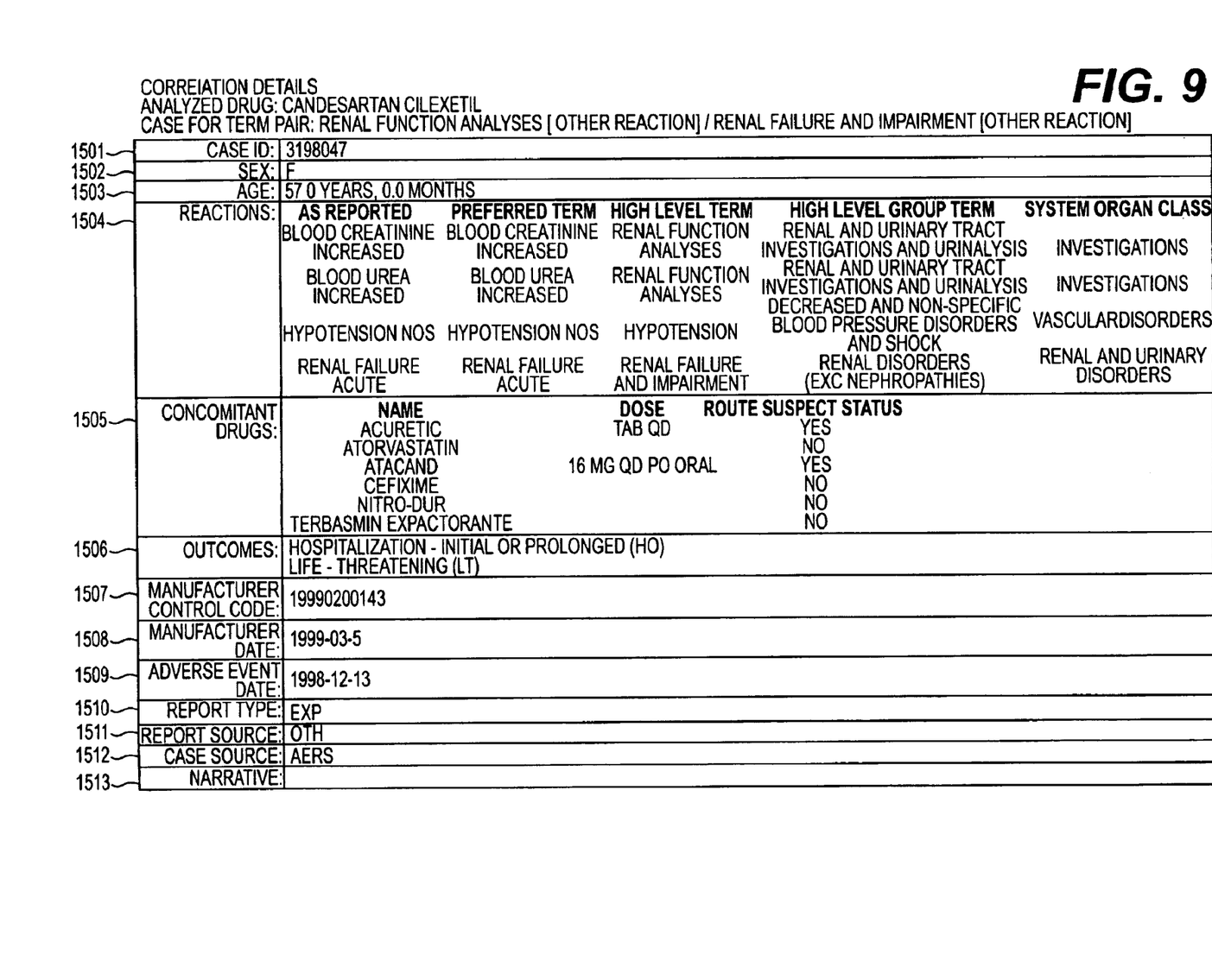
FIG. 9 illustrates mapping of source data reaction terms to reference source "map to" tokens for the MedDRA reaction hierarchy.

An exemplary screen from an illustrative embodiment of an invention disclosed in a related application is presented in FIG. 9. The screen illustrates, among other things, the nature of mapping of verbatim reaction data to the MedDRA reaction hierarchy. The verbatim data is identified under the heading "as reported," e.g., "Hypotension NOS." Subsequent columns map the verbatim to MedDRA preferred terms (e.g., Hypotension NOS), high level terms (e.g., Hypotension), high level group term (e.g., decreased and nonspecific blood pressure disorders and shock), and system/organ/class term (e.g., vascular disorders).

Preferred embodiments of the present invention include those implemented on a single computer or across a network of computers, e.g., a local area network of the Internet. Preferred embodiments include implementations on computer-readable media storing a computer program product performing one or more of the steps described herein. Such a computer program product contains modules implementing the steps as functions inter-related as described herein. Preferred embodiments of the invention include the unique data structures described herein, encoded on a computer-readable medium and computer signals transmissible over a computer/communications network.

A method and system for developing a pharmacovigilance database has been described herein. These and other variations, which will be appreciated by those skilled in the art, are within the intended scope of this invention as claimed below. As previously stated, detailed embodiments of the present invention are disclosed herein; however, it is to be understood that the disclosed embodiments are merely exemplary of the invention that may be embodied in various forms.

What is claimed is:

1. A method for developing a pharmacovigilance database from source data having verbatim terms and from reference data, wherein the source data represents a plurality of cases regarding effects experienced by persons using one or more drugs, the method comprising:

parsing the source data into a relational database;

performing cleanup on the source data stored in the relational database and storing cleaned up source data in the relational database; and mapping verbatim terms from the cleaned up source data to at least one token, the token being at least one of (1) a term from the reference data and (2) a term selected from the verbatim terms, wherein when the token is selected from the verbatim terms, the step of mapping comprises analyzing the verbatim terms contained in the plurality of cases, nominating one of the verbatim terms as a likely correct token in view of other data associated with the verbatim terms, and selecting the nominated token as the at least one token for mapping, whereby a pharmacovigilance database comprising the cleaned up source data and mapped tokens is developed.

2. A method for developing a pharamcovigilance database from source data having verbatim terms and from reference data, wherein the source data represents a plurality of cases regarding effects experienced by persons using one or more drugs, the method comprising:

performing cleanup on the source data to obtain cleaned up source data;

parsing the cleaned up source data into a relational database; and mapping verbatim terms from the cleaned up source data to at least one token, the token being at least one of (i) a term from the reference data and (2) a term selected from the verbatim terms, wherein when the token is selected from the verbatim terms, the step of mapping comprises analyzing the verbatim terms contained in the plurality of cases, nominating one of the verbatim terms as a likely correct token in view of other data associated with the verbatim terms, and selecting the nominated token as the at least one token for mapping, whereby a pharmacovigilance database comprising the cleaned up source data and mapped tokens is developed.

3. The method of claim 1, wherein parsing further comprises parsing at least one of publicly available source data and privately available source data into the relational database.

4. The method of claim 3, wherein the publicly available source data comprises at least one of Spontaneous Reporting System (SRS) data and Adverse Event Reporting System (AERS) data.

5. The method of claim 1, performing cleanup further comprises, suppressing at least one redundant entry.

6. The method of claim 1, wherein performing cleanup further comprises, suppressing printable and non-printable non-alpha characters.

7. The method of claim 1, wherein performing cleanup further comprises, suppressing numeric characters.

8. The method of claim 1, wherein performing cleanup further comprises, suppressing noise words.

9. The method of claim 1, wherein performing cleanup further comprises, suppressing combination words.

10. The method of claim 1, wherein performing cleanup further comprises, suppressing misspellings.

11. The method of claim 10, wherein suppressing misspellings further comprises:

interactively identifying likely misspelled terms to an operator;

accepting direction from an operator; and editing the likely misspelled term for which direction was accepted in accordance with the direction.

12. The method of claim 11, wherein suppressing misspellings further comprises nominating at least one correction for at least one likely misspelled term to an operator.

13. The method of claim 1, wherein performing cleanup further comprises moving at least one valid, but dislocated, entry to a proper field in the relational database for that entry.

14. The method of claim 1, wherein the other data associated with the verbatim terms comprises at least one of age, sex, dates, reaction, dose, outcomes, report sources, and concomitant drugs.

15. The method of claim 1, further comprising providing an interactive display for selecting the token.

16. The method of claim 1, further comprising displaying pedigree information generated in the course of performing the step of mapping verbatim terms to at least one token.

17. The method of claim 1, further comprising record linking to match successor case reports with predecessor case reports.

18. The method of claim 17, further comprising comparing predetermined fields in each of the reports.

19. The method of claim 1, further comprising capturing and using domain-specific lexical knowledge.

20. The method of claim 5, wherein the step of suppressing at least one redundancy comprises analyzing at least two separate cases of the plurality of cases to determine whether the at least two cases represent a single case with multiple events.

* * * * *